(12) United States Patent
Ueda et al.

(10) Patent No.: US 10,688,293 B2
(45) Date of Patent: Jun. 23, 2020

(54) MEDICAL CONNECTOR

(71) Applicant: TERUMO KABUSHIKI KAISHA, Tokyo (JP)

(72) Inventors: Yasuhiro Ueda, Kofu (JP); Takeshi Toyama, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 333 days.

(21) Appl. No.: 15/721,624

(22) Filed: Sep. 29, 2017

(65) Prior Publication Data

US 2018/0021560 A1 Jan. 25, 2018

Related U.S. Application Data

(63) Continuation of application No. PCT/JP2016/001797, filed on Mar. 28, 2016.

(30) Foreign Application Priority Data

Mar. 30, 2015 (JP) .................................. 2015-068024

(51) Int. Cl.
*A61M 39/10* (2006.01)
*A61M 39/26* (2006.01)
(Continued)

(52) U.S. Cl.
CPC ............ *A61M 39/10* (2013.01); *A61M 39/20* (2013.01); *A61M 39/24* (2013.01); *A61M 39/26* (2013.01);
(Continued)

(58) Field of Classification Search
CPC ...... A61M 39/10; A61M 39/00; A61M 39/22; A61M 39/1011; A61M 39/045;
(Continued)

(56) References Cited

U.S. PATENT DOCUMENTS 5,676,346 A * 10/1997 Leinsing ............... A61M 39/26
251/149.1
6,569,117 B1 5/2003 Ziv et al.
(Continued)

FOREIGN PATENT DOCUMENTS

JP 2008-540045 A 11/2008
JP 2012-024565 A 2/2012
(Continued)

OTHER PUBLICATIONS

International Search Report and Japanese Language Written Opinion received in PCT/JP2016/001797 dated May 17, 2016.

*Primary Examiner* — Jason E Flick
*Assistant Examiner* — Mark A Igel
(74) *Attorney, Agent, or Firm* — Foley & Lardner LLP

(57) ABSTRACT

A medical connector includes: a housing including a male connector connection portion comprising a male connector connection port having a cylindrical shape, a medical instrument connection portion, and a valve body housing portion; and a valve body configured to open and close the male connector connection port, the valve body including a head portion, and a barrel portion that connects to the head portion. When a male connector is inserted into the male connector connection port, the head portion moves from the male connector connection port into the valve body housing portion and a slit in the head portion opens, such that a flow passage from the male connector connection portion to the medical instrument connection portion is formed.

11 Claims, 12 Drawing Sheets

(51) Int. Cl.
*A61M 39/20* (2006.01)
*A61M 39/24* (2006.01)

(52) U.S. Cl.
CPC . *A61M 2039/205* (2013.01); *A61M 2039/261* (2013.01)

(58) Field of Classification Search
CPC .. A61M 39/24; A61M 39/02; A61M 39/0693; A61M 39/06; A61M 39/26; A61M 2039/205; A61M 2039/261
See application file for complete search history.

(56) References Cited

U.S. PATENT DOCUMENTS

| | | | | |
|---|---|---|---|---|
| 6,871,838 | B2* | 3/2005 | Raines | A61M 39/26 251/149 |
| 7,160,272 | B1* | 1/2007 | Eyal | A61M 39/02 604/246 |
| 9,067,049 | B2* | 6/2015 | Panian | A61M 39/22 |
| 2006/0027270 | A1* | 2/2006 | Truitt | A61M 39/02 137/843 |
| 2006/0058734 | A1* | 3/2006 | Phillips | A61M 39/26 604/93.01 |
| 2006/0163515 | A1* | 7/2006 | Ruschke | A61M 39/26 251/149.7 |
| 2007/0017583 | A1* | 1/2007 | Fangrow, Jr. | A61M 39/10 137/614.06 |
| 2007/0218745 | A1* | 9/2007 | Yokota | A61M 39/045 439/357 |
| 2008/0103484 | A1* | 5/2008 | Hishikawa | A61M 39/1011 604/533 |
| 2011/0130724 | A1* | 6/2011 | Mansour | A61M 39/26 604/256 |
| 2015/0008664 | A1* | 1/2015 | Tachizaki | A61M 39/045 285/45 |

FOREIGN PATENT DOCUMENTS

| | | |
|---|---|---|
| JP | 2012024565 A * | 2/2012 |
| JP | 2013-500453 A | 1/2013 |
| WO | WO-2009/144559 A2 | 12/2009 |

\* cited by examiner

MEDICAL CONNECTOR

CROSS-REFERENCE TO RELATED APPLICATIONS

The present application is a bypass continuation of PCT Application No. PCT/JP2016/001797, filed on Mar. 28, 2016, which claims priority to Japanese Application No. 2015-068024, filed on Mar. 30, 2015. The contents of these applications are hereby incorporated by reference in their entireties.

BACKGROUND

The present application relates to a medical connector including a housing having a male connector connection portion and a medical instrument connection portion and a valve body that opens and closes a male connector connection port of the male connector connection portion. In particular, the present application can allow for suppression of generation of discharge and suction of fluid in the medical instrument connection portion, which are caused when the male connector is inserted and removed in the male connector connection portion, and to reduce a fluid staying portion (dead space) generated in the medical connector.

As a medical connector is known that is used in, for example, various medical devices, infusion containers, and liquid feeding apparatuses, to connect to a tube body of medical instrument. For example, JP 2013-500453 W describes a medical connector including a housing having a male connector connection portion and a medical instrument connection portion and a valve body that opens and closes a male connector connection port of the male connector connection portion.

In the medical connector illustrated in FIG. 37 of JP 2013-500453 W, when a male connector is inserted into the male connector connection port, a leg portion of the valve body is shrunk and deformed, a head portion is pushed from the male connector connection port into the medical connector, and a slit provided in the head portion opens, so that a flow passage from the male connector connection portion to the medical instrument connection portion is formed.

SUMMARY

In a medical connector having a configuration as illustrated in FIG. 37 of JP 2013-500453W, when the male connector is inserted in the male connector connection portion, suction of fluid is generated in the medical instrument connection portion, and when the male connector is removed in the male connector connection portion, discharge of fluid is generated in the medical instrument connection portion. However, it is desired to suppress as much as possible the generation of discharge and suction of fluid in the medical instrument connection portion, which are caused when the male connector is inserted and removed in the male connector connection portion.

For such a medical connector, it is desired that a dead space generated in the medical connector when the male connector is connected to the male connector connection portion is minimized.

Embodiments described in this application have been developed to respond to the desires described above, and one object of certain embodiments is to provide a medical connector that suppresses generation of discharge and suction of fluid in the medical instrument connection portion, which are caused when the male connector is inserted and removed in the male connector connection portion, and reduces a dead space generated in the medical connector.

In one embodiment, a medical connector includes: a housing having a male connector connection portion and a medical instrument connection portion; and a valve body that opens and closes a male connector connection port of the male connector connection portion, wherein the housing includes a valve body housing portion, which connects to the male connector connection port having a cylindrical shape and has an inner circumferential surface having a cylindrical shape of which diameter is larger than that of the male connector connection port, the valve body has a head portion and a barrel portion that connects to the head portion, the head portion has a slit that can be opened to an upper surface and an outer circumferential surface of the head portion, and in a natural state in which no compressive force is applied to the head portion in a radial direction, a first width of the head portion, which is a width in a direction perpendicular to the slit, is greater than a second width of the head portion, which is a width in a direction along the slit, the barrel portion has a cylindrical outer circumferential surface of which outer diameter is substantially coincident with an inner diameter of an inner circumferential surface of the valve body housing portion, and when a male connector is inserted into the male connector connection port, the head portion moves from the male connector connection port into the valve body housing portion and the slit opens, so that a flow passage from the male connector connection portion to the medical instrument connection portion is formed.

In the present application, the description that the outer diameter of the cylindrical outer circumferential surface of the barrel portion of the valve body "is substantially coincident with" the inner diameter of the cylindrical inner circumferential surface of the valve body housing portion means that the outer diameter of the outer circumferential surface of the barrel portion of the valve body is within a range of 0.7 to 1.1 times the inner diameter of the inner circumferential surface of the valve body housing portion. The outer diameter is preferably within a range of 0.8 to 1.0 times the inner diameter, and more preferably within a range of 0.85 to 0.95 times the inner diameter. This is because when the outer diameter of the outer circumferential surface of the barrel portion of the valve body is smaller than 0.7 times the inner diameter of the inner circumferential surface of the valve body housing portion, a dead space generated when the male connector is inserted becomes too large and the amount of fluid discharged when the male connector is removed becomes too large, and when the outer diameter of the outer circumferential surface of the barrel portion of the valve body exceeds 1.1 times the inner diameter of the inner circumferential surface of the valve body housing portion, it is not possible to secure smooth movement of the barrel portion of the valve body in the valve body housing portion.

In one aspect, in the natural state, the first width of the head portion of the valve body is substantially coincident with a width of the barrel portion in the same direction as that of the first width.

In the present application, the description that the first width of the head portion of the valve body "is substantially coincident with" a width of the barrel portion in the same direction as that of the first width means that the width of the head portion is within a range of 0.8 to 1.4 times the width of the barrel portion. The width of the head portion is preferably within a range of 0.9 to 1.3 times the width of the barrel portion, and more preferably within a range of 1 to 1.2 times the width of the barrel portion. This is because when the width of the head portion is set to greater than or equal to 0.8 times the width of the barrel portion, it is possible to more reliably reduce the amount of fluid discharged when the male connector is removed, and when the width of the head portion is set to smaller than or equal to 1.4 times the width of the barrel portion, it is possible to reliably and sufficiently open the slit when the male connector is inserted.

In one aspect, the head portion of the valve body has an elliptical shape and the slit is formed along a short axis of the ellipse.

In one aspect, a fluid communication passage that connects to a flow passage in the medical instrument connection portion is provided outside the valve body housing portion, and a communication hole that connects to the fluid communication passage is provided in the inner circumferential surface of the valve body housing portion.

In one aspect, the slit of the valve body can open in just one location in the outer circumferential surface of the head portion, and the valve body is arranged so that the valve body does not rotate in a circumferential direction with respect to the housing and an opening portion of the slit in the outer circumferential surface of the head portion faces the communication hole when the male connector is inserted.

In one aspect, the valve body includes a ring-shaped sealing protrusion which is circularly provided along a lower end portion of the barrel portion and can slide inside the valve body housing portion.

In one aspect, the valve body includes a leg portion which connects to the barrel portion and is formed as a bellows portion that can be shrinkably deformed in the valve body housing portion.

According to certain embodiments, when the male connector is inserted into the male connector connection port, the head portion of the valve body moves from the male connector connection port into the valve body housing portion and the slit provided in the head portion opens, so that the flow passage from the male connector connection portion to the medical instrument connection portion is formed. The cylindrical outer circumferential surface of the barrel portion of the valve body has an outer diameter substantially coincident with the inner diameter of the inner circumferential surface of the valve body housing portion, so that it is possible to reduce a dead space generated between the barrel portion of the valve body and the valve body housing portion when the male connector is inserted and it is also possible to suppress generation of discharge and suction of fluid in the medical instrument connection portion, which are caused when the male connector is inserted and removed in the male connector connection portion.

Further, in certain aspects, in the natural state in which no compressive force is applied to the head portion of the valve body in the radial direction, the first width of the head portion, which is the width in the direction perpendicular to the slit, is greater than the second width of the head portion, which is the width in the direction along the slit. Therefore, when the head portion of the valve body is located in the cylindrical male connector connection port, the head portion is pressed in a direction in which the slit is closed, and the male connector connection port is closed by the head portion. When the head portion of the valve body moves from the male connector connection port into the valve body housing portion of which diameter is larger than that of the male connector connection port, the head portion tries to return to the natural state and the slit is readily opened, so that it is possible to easily form the flow passage from the male connector connection portion to the medical instrument connection portion. Therefore, it is not necessary to compress the head portion of the valve body in the vertical direction to cause the slit to open, so that it is possible to insert and remove the male connector almost without causing contraction and expansion deformation of the head portion in the vertical direction and the radial direction. As a result, it is possible to suppress variation in flow passage volume caused by elastic deformation of the head portion, and thereby it is possible to suppress generation of discharge and suction of fluid in the medical instrument connection portion, which are caused when the male connector is inserted and removed in the male connector connection portion.

Therefore, in certain embodiments, it is possible to provide a medical connector which suppresses generation of discharge and suction of fluid in the medical instrument connection portion, which are caused when the male connector is inserted and removed in the male connector connection portion, and reduces a dead space generated in the medical connector.

DETAILED DESCRIPTION

Hereinafter, a medical connector according to an embodiment of the present application will be described with reference to FIGS. 1 to 12.

Figure 1:
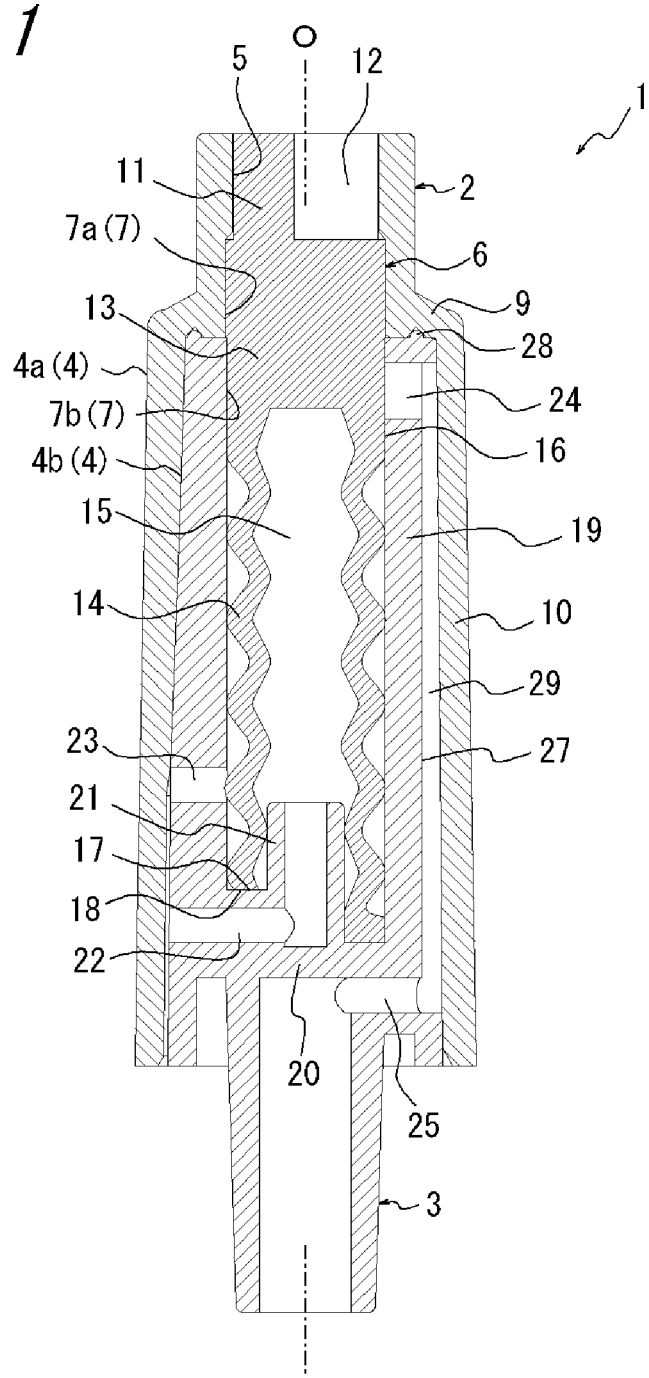
FIG. 1 is a vertical cross-sectional view of a medical connector according to an embodiment of the present invention and illustrates a state in which a male connector is not inserted.

In the present description, a vertical direction means a direction along a central axis line of a male connector connection portion of the medical connector, an upward direction means a removal direction of the male connector (that is, an upward direction in FIG. 1), and a downward direction means an insertion direction of the male connector (that is, a downward direction in FIG. 1).

Figure 2:
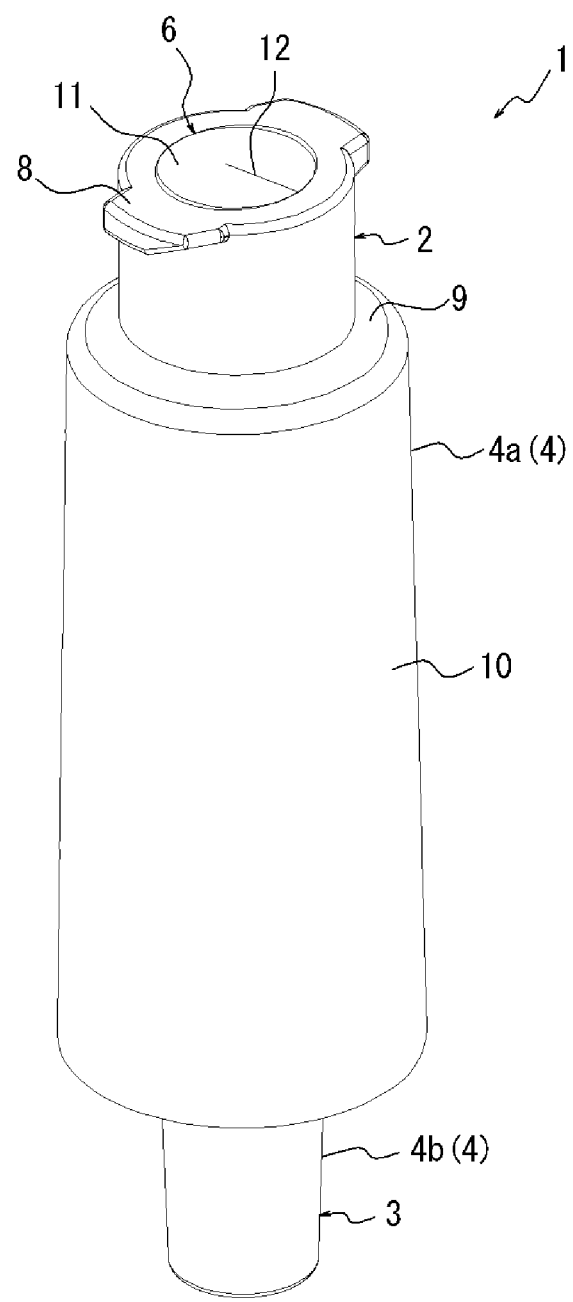
FIG. 2 is a perspective view of the medical connector illustrated in FIG. 1.
Figure 3:
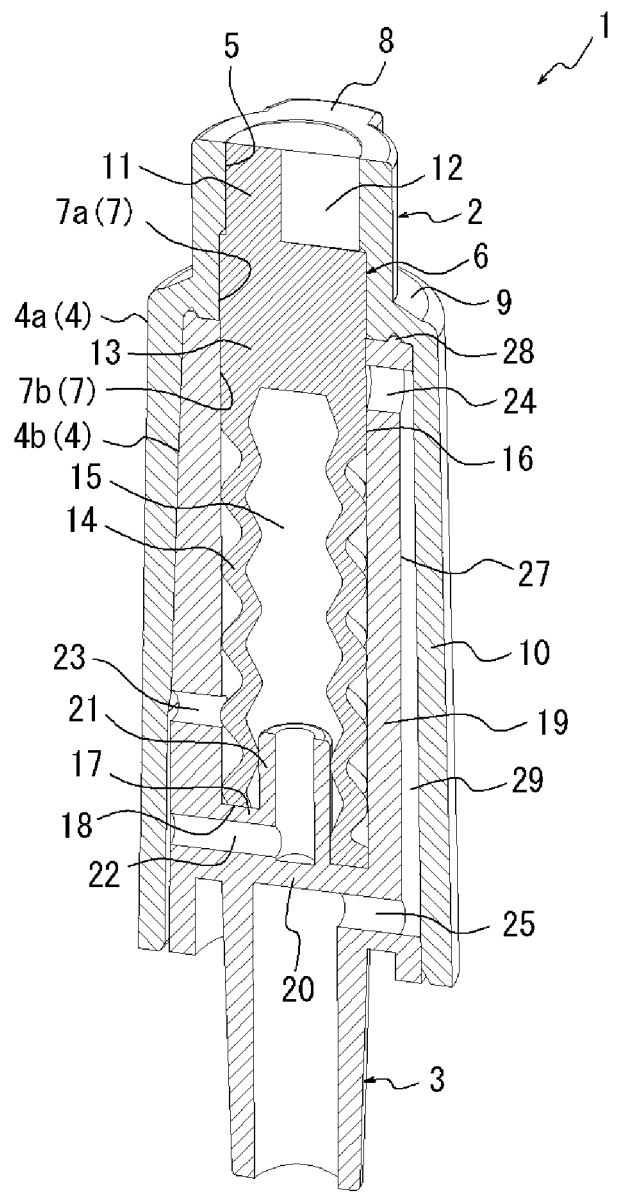
FIG. 3 is a vertical cross-sectional perspective view of the medical connector illustrated in FIG. 1.
Figure 4:
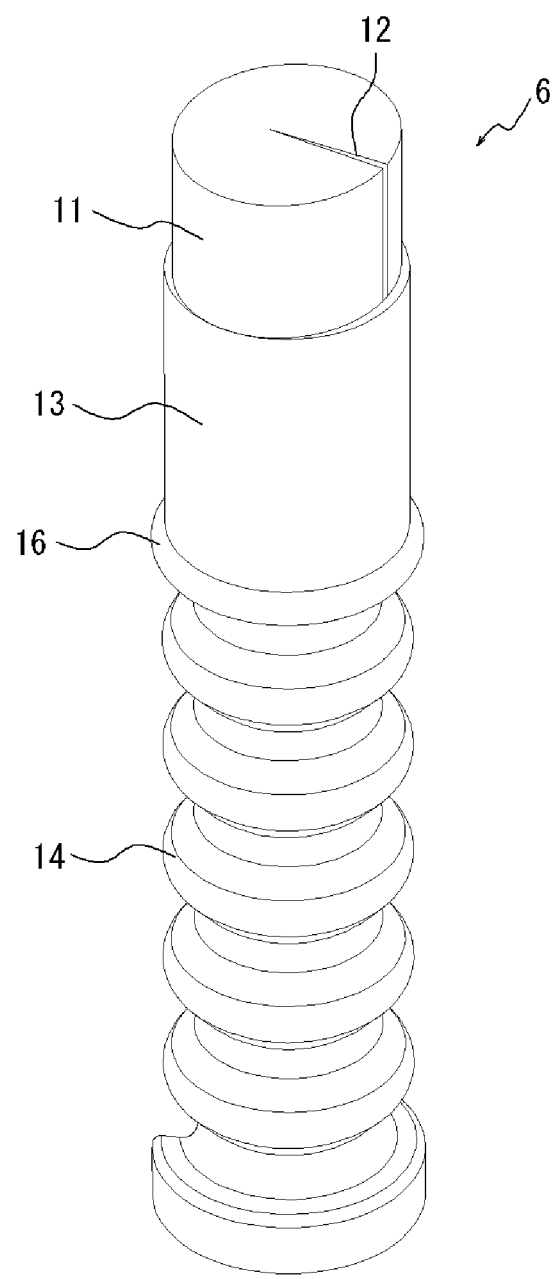
FIG. 4 is a perspective view of a valve body of the medical connector illustrated in FIG. 1 in a natural state.
Figure 5:
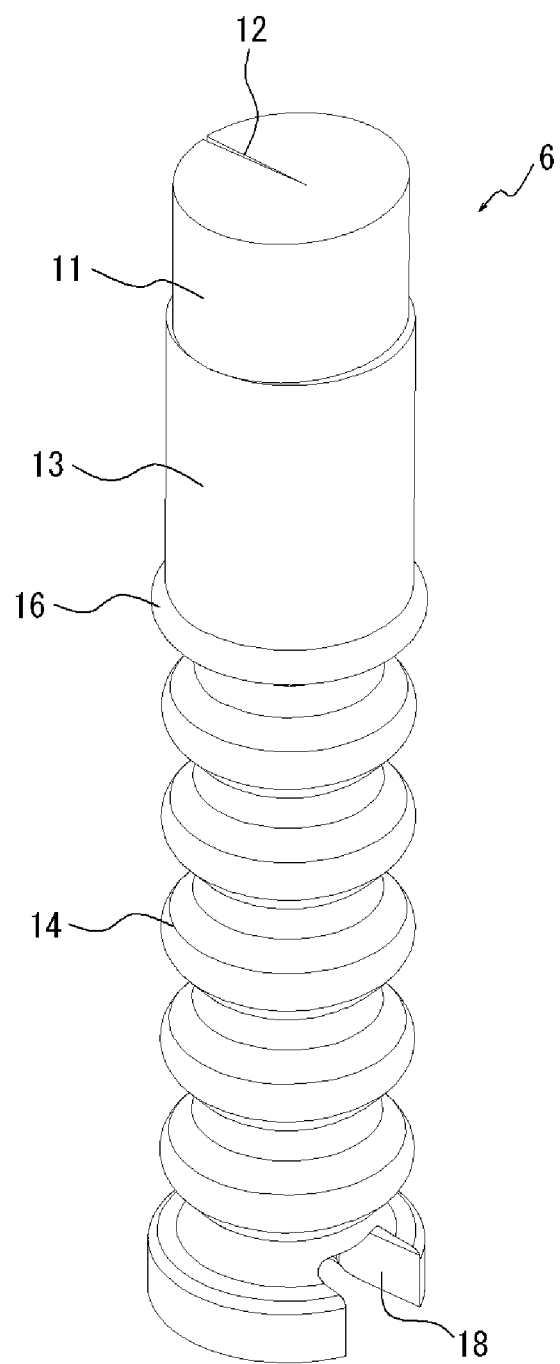
FIG. 5 is a perspective view of the valve body illustrated in FIG. 4, which is viewed from another angle, in a natural state.
Figure 6:
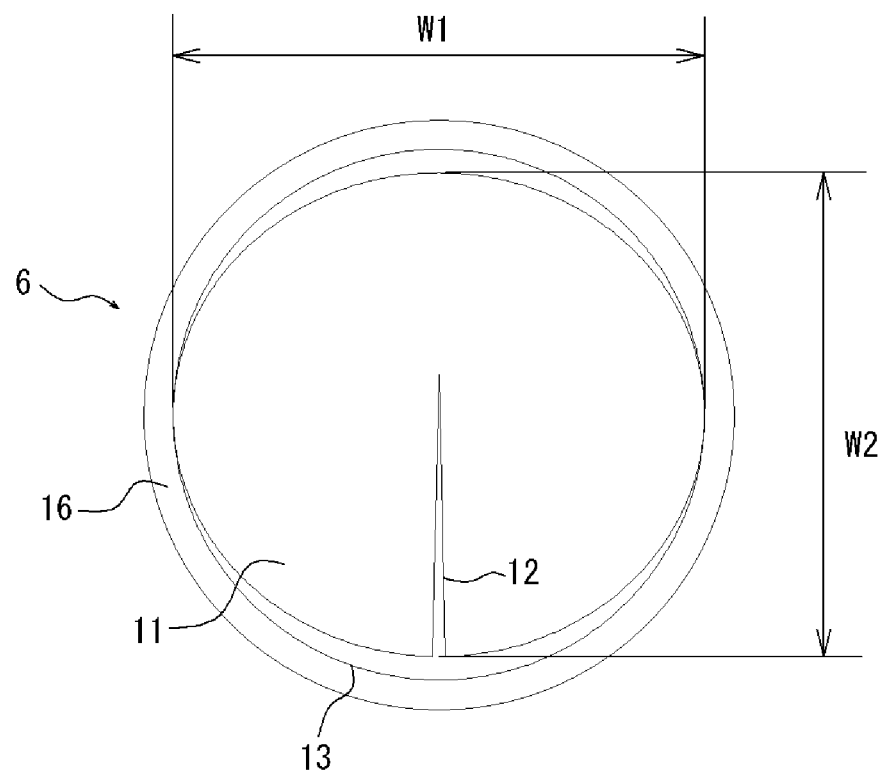
FIG. 6 is a plan view of the valve body illustrated in FIG. 4 in a natural state.
Figure 7:
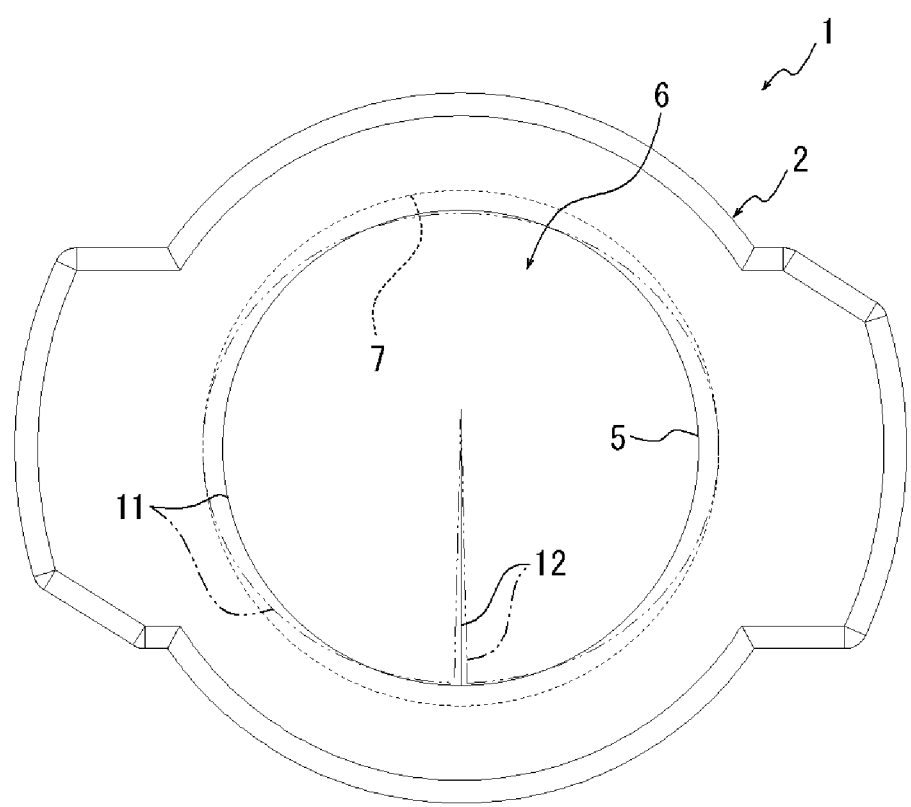
FIG. 7 is a plan view of the medical connector illustrated in FIG. 1.
Figure 8:
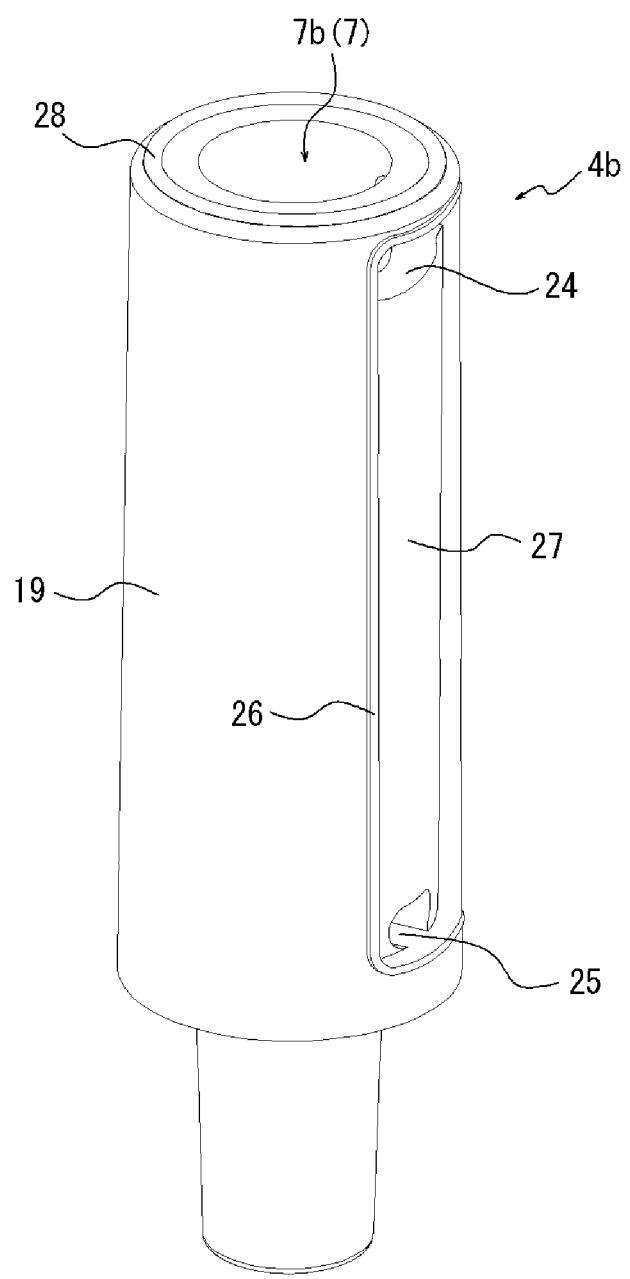
FIG. 8 is a perspective view of an inner housing of the medical connector illustrated in FIG. 1.

As illustrated in FIGS. 1 to 3, a medical connector 1 includes a housing 4 having a male connector connection portion 2 and a medical instrument connection portion 3 and a valve body 6 that opens and closes a male connector connection port 5 of the male connector connection portion 2. The housing 4 includes a valve body housing portion 7, which connects to the male connector connection port 5 having a cylindrical shape and has an inner circumferential surface having a cylindrical shape of which diameter is larger than that of the male connector connection port 5.

In the present embodiment, the housing 4 includes an outer housing 4a and an inner housing 4b. The housing 4 is formed by fixing the outer housing 4a to the inner housing 4b. The outer housing 4a and the inner housing 4b are fixed to each other by, for example, welding or bonding. When the outer housing 4a and the inner housing 4b are made of synthetic resin, they may be fixed by using, for example, thermal welding or the like. In the present example, the housing 4 is configured by two members: the outer housing 4a and the inner housing 4b. However, the housing 4 may instead be formed by, for example, one member or three members according to a manufacturing method to be employed. As a material for the valve body 6, it is preferable to use, for example, a rubber material, a thermoplastic elastomer, or the like.

An upper end portion of the outer housing 4a is the male connector connection portion 2 having a cylindrical shape with an axis line O as its center. An upper end portion 7a of the valve body housing portion 7 is formed under the male connector connection port 5 of the male connector connection portion 2. In the present example, a locking protrusion 8 for fixing a Luer lock type male connector is formed on an upper end portion of the outer circumferential surface of the male connector connection portion 2. It is possible to omit the locking protrusion 8. An outer circumferential wall portion 10 having a cylindrical shape is vertically provided from the lower end of the male connector connection portion 2 through a flange wall portion 9 extending outside in the radial direction.

As illustrated in FIGS. 1 to 7, the valve body 6 has a head portion 11 that opens and closes the cylindrical male connector connection port 5 of the male connector connection portion 2. The head portion 11 has a cylindrical shape with the axis line O as its center. The head portion 11 has a slit 12 that is opened to the upper surface and the outer circumferential surface of the head portion 11 in a natural state in which no compressive force is applied to the head portion 11 in the radial direction. Further, in the natural state, a first width W1 of the head portion 11, which is a width in a direction perpendicular to the slit 12, is greater than a second width W2 of the head portion 11, which is a width in a direction along the slit 12 (see FIG. 6).

In the present embodiment, the head portion 11 has an elliptical shape in plan view in the natural state and the slit 12 is formed along the short axis of the ellipse. As illustrated by a solid line in FIG. 7, when the head portion 11 is located in the cylindrical male connector connection port 5, the inner diameter of the male connector connection port 5 is smaller than the first width W1, so that the head portion 11 is compressed in the radial direction by the male connector connection port 5 and the slit 12 is closed. On the other hand, when the head portion 11 moves from the male connector connection port 5 into the valve body housing portion 7, as illustrated by a dot-dot-dash line in FIG. 7, the head portion 11 tries to return to the natural state, so that the slit 12 opens.

A barrel portion 13 having a cylindrical outer circumferential surface is connected to the head portion 11. In the natural state, the first width W1 of the head portion 11 is substantially coincident with a width of the barrel portion 13 (that is, a diameter of the cylindrical barrel portion 13) in the same direction as that of the first width W1 (in the present embodiment, the width of the head portion 11 is one times the width of the barrel portion 13).

The barrel portion 13 has a cylindrical outer circumferential surface of which outer diameter is substantially coincident with an inner diameter of the inner circumferential surface of the valve body housing portion 7. More specifically, in the present embodiment, the outer diameter of the outer circumferential surface of the barrel portion 13 is 4.4 mm and the inner diameter of the inner circumferential surface of the valve body housing portion 7 is 4.8 mm, so that the outer diameter of the outer circumferential surface of the barrel portion 13 is 0.91 times the inner diameter of the inner circumferential surface of the valve body housing portion 7. In FIGS. 1, 3, 7, and 12, a gap between the outer circumferential surface of the barrel portion 13 and the inner circumferential surface of the valve body housing portion 7 is omitted. In the present embodiment, the barrel portion 13 is connected with a leg portion 14 that is formed as a bellows portion that can be shrinkably deformed in the valve body housing portion 7. The inside of the leg portion 14 formed as the bellows portion is a hollow portion 15 that opens to an end portion opposite to the head portion 11. In an upper end portion of the leg portion 14, a ring-shaped sealing protrusion 16 is provided which is circularly provided along the lower end portion of the barrel portion 13 and can slide inside the valve body housing portion 7. In a lower end portion of the leg portion 14, a recessed portion 18 that engages with a protruded portion 17 formed in the valve body housing portion 7 and inhibits a rotation of the valve body 6 in the circumferential direction is formed.

As illustrated in FIGS. 1, 3, and 8 to 10, in the inner housing 4b, a portion 7b is formed which is a portion of the valve body housing portion 7 other than the upper end portion 7a of the valve body housing portion 7. The portion 7b is partitioned by an inner circumferential surface of an inner circumferential wall portion 19 having a cylindrical shape with an axis line O as its center and an upper surface of a bottom wall portion 20 that connects to a lower end portion of the inner circumferential wall portion 19. On the center of upper surface of the bottom wall portion 20, an insertion protrusion 21 is formed that protrudes upward and is inserted into the hollow portion 15 of the valve body 6. Further, on the upper surface of the bottom wall portion 20, the protruded portion 17 is formed that engages with the recessed portion 18 of the valve body 6 described above and inhibits a circumferential rotation of the valve body 6.

In the insertion protrusion 21 and the protruded portion 17, a first air passage 22 is formed that connects the hollow portion 15 of the valve body 6 to a space outside the inner circumferential wall portion 19. Further, in the inner circumferential wall portion 19, a second air passage 23 is formed that connects a space partitioned by the inner circumferential surface of the valve body housing portion 7 and the outer circumferential surface of the leg portion 14 of the valve body 6 to the space outside the inner circumferential wall portion 19. Each of the first air passage 22 and the second air passage 23 connects to a space outside the medical connector 1 through a gap between the inner circumferential wall portion 19 and the outer circumferential wall portion 10 of the outer housing 4a.

In the inner circumferential surface of the inner circumferential wall portion 19, a communication hole 24 that penetrates to the outer circumference side of the inner circumferential wall portion 19 is provided. Further, the medical instrument connection portion 3 is formed in a lower portion of the bottom wall portion 20. In a lower end portion of the inner circumferential wall portion 19, a through hole 25 is formed that connects a flow passage in the medical instrument connection portion 3 to a space on the outer circumference side of the inner circumferential wall portion 19. Both of the communication hole 24 and the through hole 25 are surrounded by a sealing protrusion 26 having a substantially rectangular shape (see FIG. 8). The inside of the sealing protrusion 26 is formed as a recessed groove portion 27 that is recessed from the outside of the sealing protrusion 26. A ring-shaped sealing protrusion 28 is circularly provided on an upper end edge portion of the inner circumferential wall portion 19. The sealing protrusions 26 and 28 may be formed as separate members made of an elastic material such as a rubber and a thermoplastic elastomer and bonded to the inner circumferential wall portion 19 or may be formed integrally with the inner circumferential wall portion 19 made of a synthetic resin by insert molding or the like.

In this way, in the present embodiment, a fluid communication passage 29 (formed by a communication passage partitioned by the recessed groove portion 27 and the outer circumferential wall portion 10 and the through hole 25) that connects to the flow passage in the medical instrument connection portion 3 is provided outside the valve body housing portion 7, and the communication hole 24 that connects to the fluid communication passage 29 is provided in the inner circumferential surface of the valve body housing portion 7.

Figure 12:
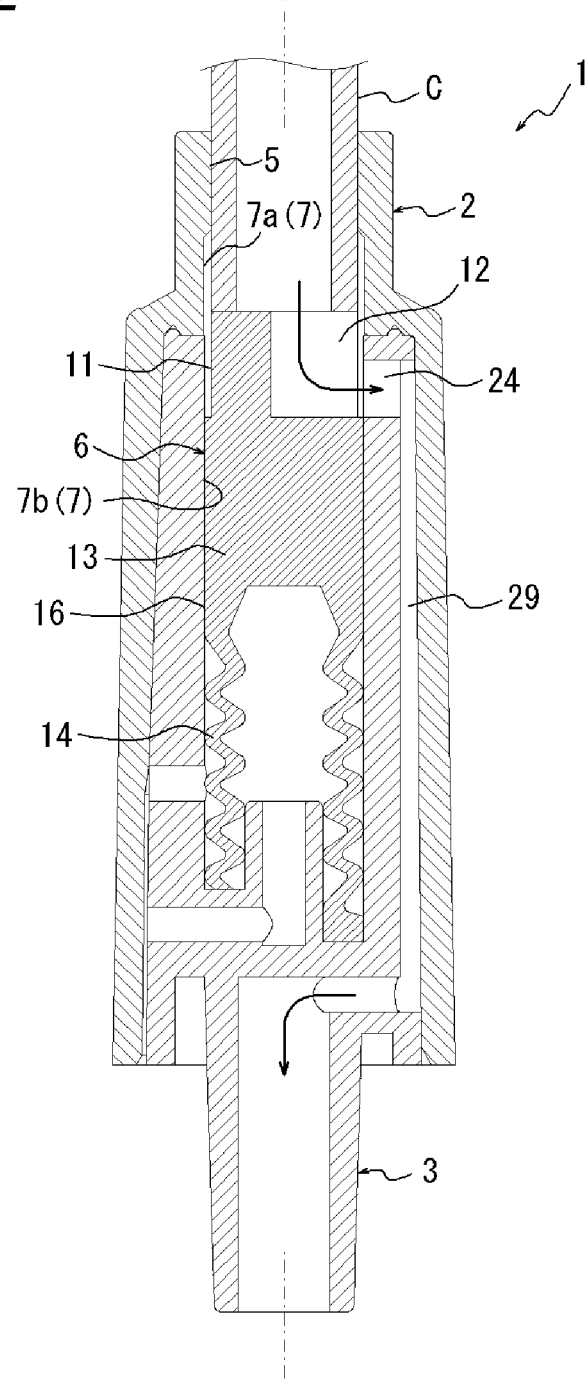
FIG. 12 is a vertical cross-sectional view of the medical connector illustrated in FIG. 1 and illustrates a state in which a male connector is inserted.

In the present embodiment, the slit 12 of the valve body 6 opens in just one location in the outer circumferential surface of the head portion 11 in the natural state, and the valve body 6 is arranged so that the valve body 6 is inhibited from rotating in the circumferential direction with respect to the housing 4 by the engagement between the protruded portion 17 and the recessed portion 18 described above and an opening portion of the slit 12 in the outer circumferential surface of the head portion 11 faces the communication hole 24 when a male connector C is inserted (see FIG. 12).

Figure 9:
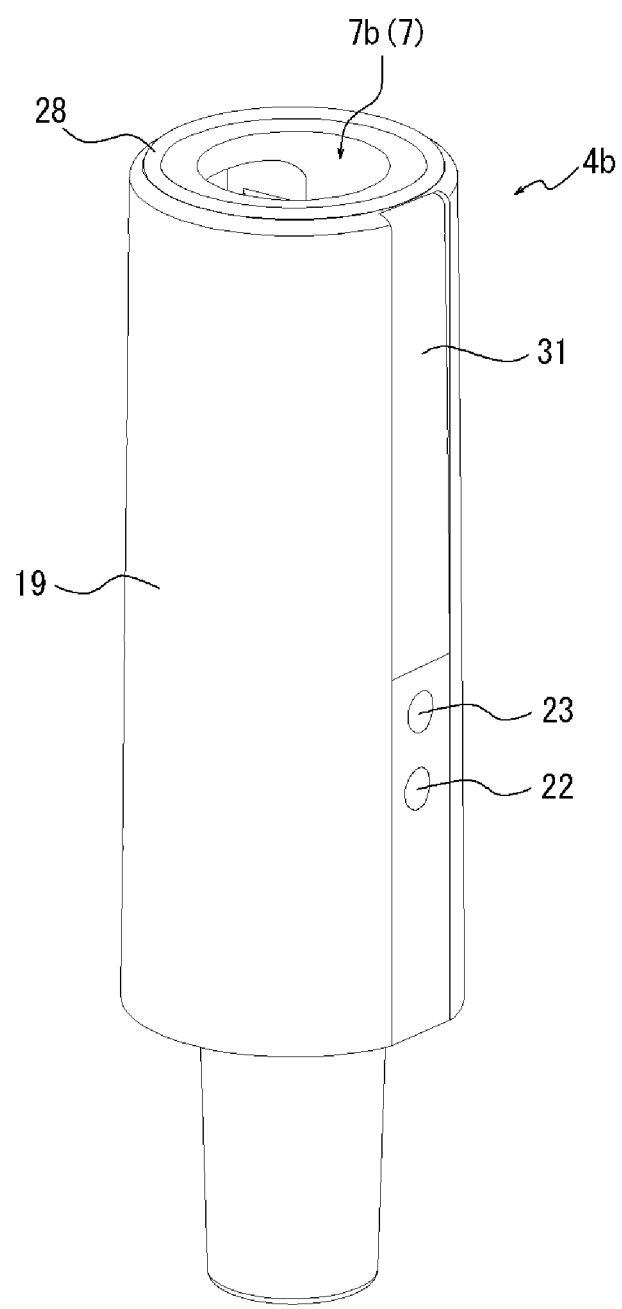
FIG. 9 is a perspective view of the inner housing illustrated in FIG. 8, which is viewed from another angle.
Figure 10:
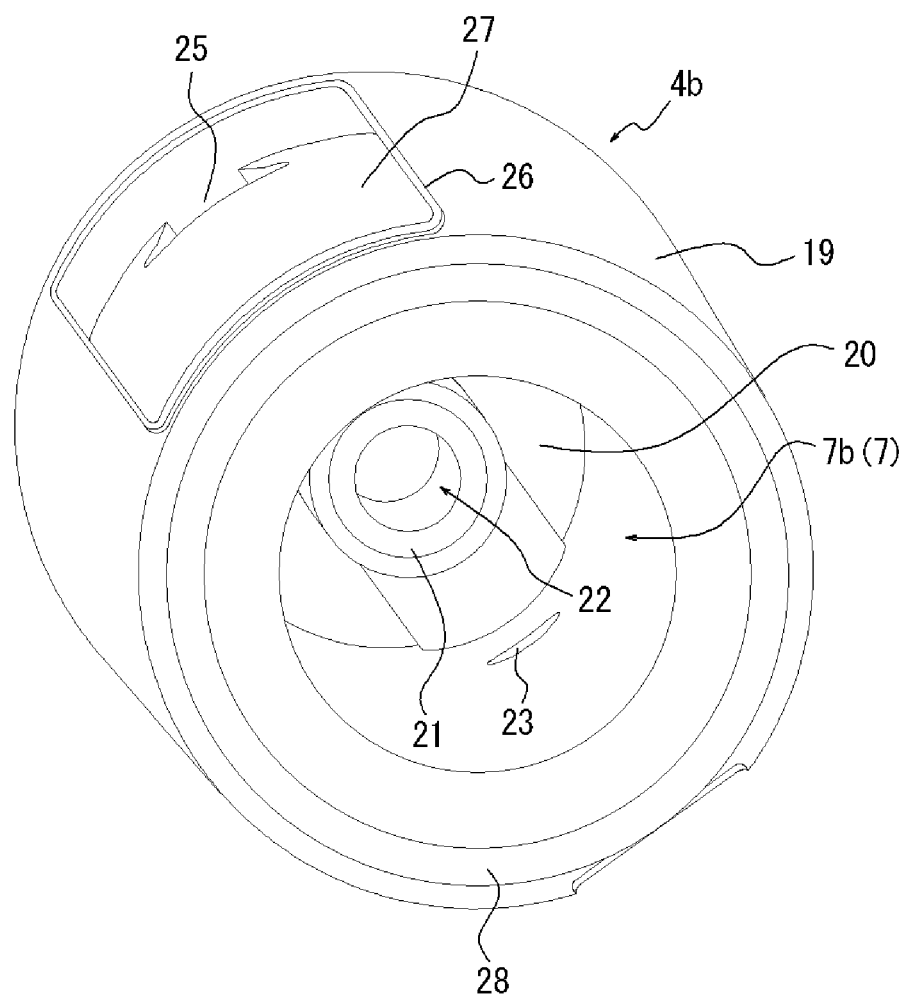
FIG. 10 is a perspective view of the inner housing illustrated in FIG. 8, which is viewed from further another angle.
Figure 11:
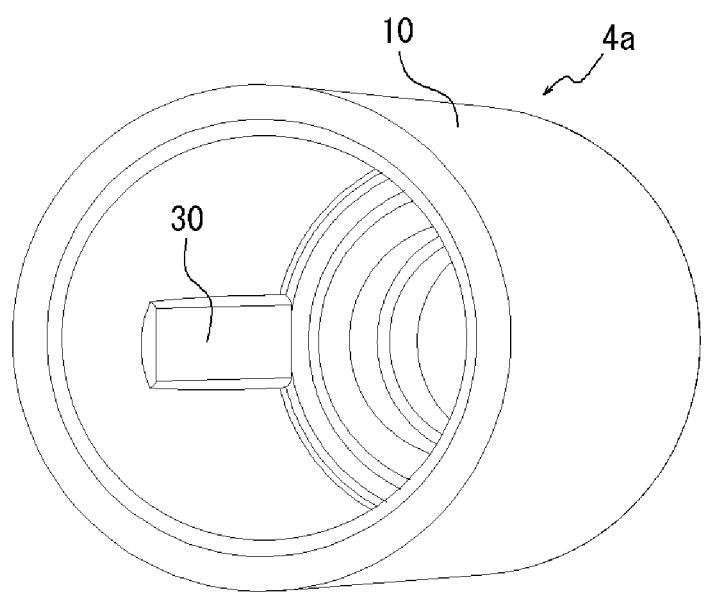
FIG. 11 is a perspective view of an outer housing of the medical connector illustrated in FIG. 1.

In the present embodiment, as illustrated in FIG. 11, a positioning protrusion 30 is formed on an inner circumferential surface of the outer circumferential wall portion 10 of the outer housing 4a, and the positioning protrusion 30 engages with a positioning recessed portion 31 illustrated in FIG. 9.

As described above, the medical connector 1 according to the present embodiment includes the housing 4 having the male connector connection portion 2 and the medical instrument connection portion 3 and the valve body 6 that opens and closes the male connector connection port 5 of the male connector connection portion 2. The housing 4 includes the valve body housing portion 7, which connects to the male connector connection port 5 having a cylindrical shape and has an inner circumferential surface having a cylindrical shape of which diameter is larger than that of the male connector connection port 5. The valve body 6 has the head portion 11 and the barrel portion 13 that connects to the head portion 11. The head portion 11 has the slit 12 that is opened to the upper surface and the outer circumferential surface of the head portion 11 in the natural state in which no compressive force is applied to the head portion 11 in the radial direction. Further, in the natural state, the first width W1 of the head portion 11, which is the width in the direction perpendicular to the slit 12, is greater than the second width W2 of the head portion 11, which is the width in the direction along the slit 12. The barrel portion 13 has a cylindrical outer circumferential surface of which outer diameter is substantially coincident with the inner diameter of the inner circumferential surface of the valve body housing portion 7.

As illustrated in FIG. 12, the medical connector 1 is configured so that when the male connector C is inserted into the male connector connection port 5, the head portion 11 moves from the male connector connection port 5 into the valve body housing portion 7 and the slit 12 opens (see the dot-dot-dash line in FIG. 7), so that a flow passage from the male connector connection portion 2 to the medical instrument connection portion 3 is formed.

Therefore, according to the medical connector 1 of the present embodiment, the cylindrical outer circumferential surface of the barrel portion 13 of the valve body 6 has substantially the same outer diameter as that of the inner diameter of the inner circumferential surface of the valve body housing portion 7, so that it is possible to reduce a dead space generated between the barrel portion 13 of the valve body 6 and the valve body housing portion 7 when the male connector C is inserted and it is also possible to suppress generation of discharge and suction of fluid in the medical instrument connection portion 3, which are caused when the male connector C is inserted and removed in the male connector connection portion 2.

Further, according to the medical connector 1 of the present embodiment, in the natural state in which no compressive force is applied to the head portion 11 of the valve body 6 in the radial direction, the first width W1 of the head portion 11, which is a width in the direction perpendicular to the slit 12, is greater than the second width W2 of the head portion 11, which is a width in the direction along the slit 12, so that when the head portion 11 of the valve body 6 is located in the cylindrical male connector connection port 5, the slit 12 closes and the male connector connection port 5 is closed by the head portion 11. When the head portion 11 of the valve body 6 moves from the male connector connection port 5 into the valve body housing portion 7 of which diameter is larger than that of the male connector connection port 5, the head portion 11 tries to return to the natural state, so that the slit 12 opens and a flow passage from the male connector connection portion 2 to the medical instrument connection portion 3 is formed.

Therefore, it is not necessary to compress the head portion 11 of the valve body 6 in the vertical direction to cause the slit 12 to open, so that it is possible to insert and remove the male connector C almost without causing contraction and expansion deformation of the head portion 11 in the vertical direction and the radial direction. As a result, it is possible to suppress variation in flow passage volume caused by elastic deformation of the head portion 11, and thereby it is possible to suppress generation of discharge and suction of fluid in the medical instrument connection portion 3, which are caused when the male connector C is inserted and removed in the male connector connection portion 2.

Further, in the medical connector 1 according to the present embodiment, in the natural state, the first width W1 of the head portion 11 of the valve body 6 is substantially coincident with the width of the barrel portion 13 in the same direction as that of the first width W1, so that the first width W1 and the inner diameter of the inner circumferential surface of the valve body housing portion 7 are substantially coincident with each other. Therefore, it is possible to more reliably reduce the amount of fluid discharged when the male connector C is removed and it is also possible to more reliably cause the slit 12 to open sufficiently when the male connector C is inserted.

Further, in the medical connector 1 according to the present embodiment, the head portion 11 of the valve body 6 has an elliptical shape and the slit 12 is formed along the short axis of the ellipse, so that while it is possible to secure a smooth opening-closing operation of the male connector connection port 5 by the head portion 11, it is also possible to effectively suppress generation of discharge and suction of fluid in the medical instrument connection portion 3, which are caused when the male connector C is inserted and removed in the male connector connection portion 2.

Further, in the medical connector 1 according to the present embodiment, the fluid communication passage 29 that connects to the flow passage in the medical instrument connection portion 3 is provided outside the valve body housing portion 7 and the communication hole 24 that connects to the fluid communication passage 29 is provided in the inner circumferential surface of the valve body housing portion 7, so that it is possible to minimize the influence of deformation of the valve body 6 with respect to the flow passage volume in the medical connector 1 and it is also possible to further suppress generation of discharge and suction of fluid in the medical instrument connection portion 3, which are caused when the male connector C is inserted and removed in the male connector connection portion 2.

Further, in the medical connector 1 according to the present embodiment, the slit 12 of the valve body 6 opens in just one location in the outer circumferential surface of the head portion 11 in the natural state, and the valve body 6 is arranged so that the valve body 6 is inhibited from rotating in the circumferential direction with respect to the housing 4 and the opening portion of the slit 12 in the outer circumferential surface of the head portion 11 faces the communication hole 24 when the male connector C is inserted. Therefore, it is possible to more reliably and smoothly flow the fluid when the male connector C is inserted.

Further, in the medical connector 1 according to the present embodiment, the valve body 6 includes a ring-shaped sealing protrusion 16 which is circularly provided along the lower end portion of the barrel portion 13 and can slide inside the valve body housing portion 7, so that it is possible to inhibit fluid from going beyond the lower end portion of the barrel portion 13 and flowing into a bottom portion of the valve body housing portion 7 and suppress generation of contamination in the bottom portion.

Further, in the medical connector 1 according to the present embodiment, the valve body 6 includes the leg portion 14 which connects to the barrel portion 13 and is formed as a bellows portion that can be shrinkably deformed in the valve body housing portion 7, so that it is possible to more reliably suppress contraction deformation and expansion deformation of the head portion 11 in the vertical direction and the radial direction, which are caused when the male connector C is inserted and removed in the male connector connection portion 2. Therefore, it is possible to more reliably suppress generation of discharge and suction of fluid.

Further, in the medical connector 1 according to the present embodiment, it is described that the slit 12 of the valve body 6 is opened to the upper surface and the outer circumferential surface of the head portion 11 in the natural state. However, the slit 12 does not necessarily need to have such a structure, and even if the slit is not opened in the natural state, the slit only has to be opened by being deformed at a level where there is almost no generation of discharge and suction of fluid when the male connector C is inserted into the male connector connection port 5. For example, in the medical connector 1, by adjusting a protrusion length of the insertion protrusion 21 that protrudes upward from the bottom wall portion 20 of the inner housing 4b, when the male connector C is inserted into the male connector connection port 5, the barrel portion 13 of the valve body 6 comes into contact with the insertion protrusion 21 and the slit may be opened.

While certain embodiments are described above, the invention is not limited to the described embodiments, and various modifications may be made without departing from the spirit of the present invention.

REFERENCE NUMERAL LIST

1 Medical connector
2 Male connector connection portion
3 Medical instrument connection portion
4 Housing
4a Outer housing
4b Inner housing
5 Male connector connection port
6 Valve body
7 Valve body housing portion
7a Upper end portion of the valve body housing portion
7b Portion of the valve body housing portion other than the upper end portion of the valve body housing portion
8 Locking protrusion
9 Flange wall portion
10 Outer circumferential wall portion
11 Head portion
12 Slit
13 Barrel portion
14 Leg portion
15 Hollow portion
16 Sealing protrusion
17 Protruded portion
18 Recessed portion
19 Inner circumferential wall portion
20 Bottom wall portion
21 Insertion protrusion
22 First air passage
23 Second air passage
24 Communication hole
25 Through hole
26 Sealing protrusion
27 Recessed groove portion
28 Sealing protrusion
29 Fluid communication passage
30 Positioning protrusion
31 Positioning recessed portion
O Axis line
C Male connector
W1 First width
W2 Second width

What is claimed is:
1. A medical connector comprising:
a housing comprising:
a male connector connection portion comprising a male connector connection port having a cylindrical shape,
a medical instrument connection portion,
a valve body housing portion,
an outer circumferential wall portion located outside of the valve body housing portion, a fluid communication passage located between the valve body housing portion and the outer circumferential wall portion, and a communication hole that is located in an inner circumferential surface of the valve body housing portion and that connects to the fluid communication passage; and a valve body configured to open and close the male connector connection port, the valve body comprising:

a head portion, and a barrel portion that connects to the head portion, wherein the valve body housing portion connects to the male connector connection port, and has an the inner circumferential surface of the valve body housing portion has having a cylindrical shape with an inner diameter that is larger than a diameter of the male connector connection port, wherein the head portion of the valve has a slit that extends along an upper surface and an outer circumferential surface of the head portion, wherein the head portion has a first width in a first direction perpendicular to the slit, and a second width in a second direction parallel to the slit, and wherein, in a natural state in which no compressive force is applied to the head portion in a radial direction, the first width of the head portion, which is a width in a direction perpendicular to the slit, is greater than the second width of the head portion, which is a width in a direction along the slit, wherein the barrel portion has a cylindrical outer circumferential surface with an outer diameter that is substantially coincident with the inner diameter of that contacts the inner circumferential surface of the valve body housing portion, and wherein the medical connector is configured such that, when a male connector is inserted into the male connector connection port, the head portion moves from the male connector connection port into the valve body housing portion and the slit opens, such that a flow passage from the male connector connection portion, through the fluid communication passage, to the medical instrument connection portion is formed.

2. The medical connector according to claim 1, wherein, in the natural state, the first width of the head portion of the valve body is substantially coincident with a width of the barrel portion in the same direction as that of the first width.

3. The medical connector according to claim 1, wherein the head portion of the valve body has a shape of an ellipse and the slit is formed along a short axis of the ellipse.

4. The medical connector according to claim 2, wherein the head portion of the valve body has a shape of an ellipse and the slit is formed along a short axis of the ellipse.

5. The medical connector according to claim 1, wherein:
the slit of the valve body is openable in only one location in the outer circumferential surface of the head portion, and the valve body is configured such that, when the male connector is inserted, the valve body does not rotate in a circumferential direction with respect to the housing and an opening portion of the slit in the outer circumferential surface of the head portion is configured to direct fluid flow towards the communication hole.

6. The medical connector according to claim 2, wherein:
the slit of the valve body is openable in only one location in the outer circumferential surface of the head portion, and the valve body is configured such that, when the male connector is inserted, the valve body does not rotate in a circumferential direction with respect to the housing and an opening portion of the slit in the outer circumferential surface of the head portion is configured to direct fluid flow towards the communication hole.

7. The medical connector according to claim 4, wherein:
the slit of the valve body is openable in only one location in the outer circumferential surface of the head portion, and the valve body is configured such that, when the male connector is inserted, the valve body does not rotate in a circumferential direction with respect to the housing and an opening portion of the slit in the outer circumferential surface of the head portion is configured to direct fluid flow towards the communication hole.

8. The medical connector according to claim 3, wherein:
the slit of the valve body is openable in only one location in the outer circumferential surface of the head portion, and the valve body is configured such that, when the male connector is inserted, the valve body does not rotate in a circumferential direction with respect to the housing and an opening portion of the slit in the outer circumferential surface of the head portion is configured to direct fluid flow towards the communication hole.

9. The medical connector according to claim 1, wherein the valve body comprises a ring-shaped sealing protrusion that is located along a lower end portion of the barrel portion and is slidable inside the valve body housing portion.

10. The medical connector according to claim 1, wherein the valve body comprises a leg portion that connects to the barrel portion and is formed as a bellows portion that can be shrinkably deformed in the valve body housing portion.

11. A method of using a medical connector, the method comprising:
Providing the medical connector, which comprises:
a housing comprising:
a male connector connection portion comprising a male connector connection port having a cylindrical shape,
a medical instrument connection portion,
a valve body housing portion,
an outer circumferential wall portion located outside of the valve body housing portion,
a fluid communication passage located between the valve body housing portion and the outer circumferential wall portion, and
a communication hole that is located in an inner circumferential surface of the valve body housing portion and that connects to the fluid communication passage; and
a valve body configured to open and close the male connector connection port, the valve body comprising:
a head portion, and
a barrel portion that connects to the head portion,
wherein the valve body housing portion connects to the male connector connection port, and has an the inner circumferential surface of the valve body housing portion has having a cylindrical shape with an inner diameter that is larger than a diameter of the male connector connection port,
wherein the head portion of the valve has a slit that extends along an upper surface and an outer circumferential surface of the head portion, wherein the head portion has a first width in a first direction perpendicular to the slit, and a second width in a second direction parallel to the slit, and wherein, in a natural state in which no compressive force is applied to the head portion in a radial direction, the first width of the head portion, is greater than the second width of the head portion, and wherein the barrel portion has a cylindrical outer circumferential surface that contacts the inner circumferential surface of the valve body housing portion, and wherein the medical connector is configured such that, when a male connector is inserted into the male connector connection port, the head portion moves from the male connector connection port into the valve body housing portion and the slit opens, such that a flow passage from the male connector connection portion, through the fluid communication passage, to the medical instrument connection portion is formed.

* * * * *

UNITED STATES PATENT AND TRADEMARK OFFICE
CERTIFICATE OF CORRECTION

PATENT NO. : 10,688,293 B2
APPLICATION NO. : 15/721624
DATED : June 23, 2020
INVENTOR(S) : Yasuhiro Ueda and Takeshi Toyama It is certified that error appears in the above-identified patent and that said Letters Patent is hereby corrected as shown below:

In the Claims

Claim 1, Column 11, Line 14:
Please delete "has an".

Claim 1, Column 11, Line 16:
Please delete "having".

Claim 1, Column 11, Lines 27-28:
Please delete ", which is a width in a direction perpendicular to the slit,".

Claim 1, Column 11, Line 29-30:
Please delete ", which is a width in a direction along the slit,".

Claim 1, Column 11, Lines 32-33:
Please delete "with an outer diameter that is substantially coincident with the inner diameter of".

Claim 11, Column 12, Line 38:
Please delete "Providing" and insert --providing--.

Claim 11, Column 12, Line 60:
Please delete "has an".

Claim 11, Column 12, Line 62:
Please delete "having".

Claim 11, Column 13, Line 6:
Please delete "the head portion, is" and insert --the head portion is--.

Signed and Sealed this
Eighth Day of September, 2020

Andrei Iancu
*Director of the United States Patent and Trademark Office*